United States Patent [19]

Kagiya et al.

[11] Patent Number: 5,304,654
[45] Date of Patent: Apr. 19, 1994

[54] FLUORINE-CONTAINING NITROIMIDAZOLE COMPOUNDS

[75] Inventors: Tsutomu Kagiya; Mitsuyuki Abe, both of Kyoto; Seiichi Nishimoto, Nara; Yuta Shibamoto, Kyoto; Kazuhiro Shimokawa, Osaka; Yorisato Hisanaga, Osaka; Tatsuo Nakada, Osaka; Toru Yoshizawa, Osaka, all of Japan

[73] Assignees: Yasunori Nishijima, Kyoto; Daikin Industries, Ltd., Osaka, both of Japan

[21] Appl. No.: 759,118

[22] Filed: Sep. 9, 1991

Related U.S. Application Data

[63] Continuation of Ser. No. 281,855, Dec. 9, 1988, abandoned, which is a continuation-in-part of Ser. No. 204,367, Jun. 9, 1988, Pat. No. 4,927,941.

[30] Foreign Application Priority Data

| Jun. 10, 1987 | [JP] | Japan | 62-147459 |
| Jun. 24, 1987 | [JP] | Japan | 62-156787 |
| Sep. 26, 1987 | [JP] | Japan | 62-241574 |
| Dec. 10, 1987 | [JP] | Japan | 62-314686 |
| Jan. 29, 1988 | [JP] | Japan | 63-20456 |
| Mar. 31, 1988 | [JP] | Japan | 63-79230 |

[51] Int. Cl.$^5$ .................. C07D 233/91; A61K 31/415
[52] U.S. Cl. .............................................. 548/327.5
[58] Field of Search ................. 548/338, 339, 327.5

[56] References Cited

U.S. PATENT DOCUMENTS

| 4,371,540 | 2/1983 | Lee et al. ............... 548/338 |
| 4,977,273 | 11/1990 | Kagiya et al. ............ 548/327.5 |

FOREIGN PATENT DOCUMENTS

| 0000928 | 3/1979 | European Pat. Off. ........... 548/338 |
| 0095906 | 12/1983 | European Pat. Off. ........... 548/338 |
| 0212558 | 3/1987 | European Pat. Off. ........... 548/338 |
| 0316967 | 5/1989 | European Pat. Off. ........... 548/327.5 |
| 0373630 | 6/1990 | European Pat. Off. ........... 548/327.5 |
| 194019 | 6/1986 | Japan ............................. 548/338 |
| 12763 | 1/1987 | Japan ............................. 548/338 |

OTHER PUBLICATIONS

Kagakuno Ryoiki (Chemical Fields), 35, 441 (1981).
Gan to Kagkuryoho, 8, (11), Nov. 1981, p. 1659.
Int. J. Radiat. Biol., 19, 575–585, 1971.
Int. J. Radiat. Biol., 35, 151–160, 1979.
Chemical Abstracts, vol. 107, No. 9, (1987), p. 73465t Mathias et al.
Chemical Abstracts, vol. 89, No. 23, (1978), p. 191005a Rauth et al.
Chemical Abstracts, vol. 89, Chem. Substance Index. I-Po, p. 2720CS.
Chemical Abstracts, vol. 89, No. 23, (1978), p. 191006b Brown et al.
Chemical Abstracts, vol. 105, No. 18, (1986), p. 160447r Jerabeh et al II.
Patent Abstracts of Japan, vol. 11, No. 18 (C-398 [2465], 17h Jan. 1987.
Patent Abstracts of Japan, vol. 9, No. 211 (C-300) [1934], 29th Aug. 1985.

(List continued on next page.)

*Primary Examiner*—Floyd D. Higel
*Attorney, Agent, or Firm*—Birch, Stewart, Kolasch & Birch

[57] ABSTRACT

A 2-nitroimidazole compound of the formula:

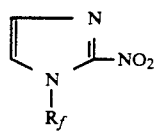

(i)

wherein $R_f$ is a fluorine-containing organic group which has at least one fluorine atom on a carbon atom which bonds to the nitrogen atom of the imidazole ring or a carbon atom which bonds to said carbon atom and a radiosensitizer comprising said nitroimidazole derivative.

1 Claim, 2 Drawing Sheets

OTHER PUBLICATIONS

Chemical Abstracts, vol. 105, No. 15, (1986), p. 130194p Raleigh et al.

Chemical Abstracts, 89:191005a, "Testing of hypoxic cell radiosensitizers in vivo", vol. 89, No. 23, Dec. 4, 1978.

Chemical Abstracts, 89:191006b, "In vivo evaluation of the radiosensitizing and cytotoxic properties of newly synthesized electron-affinic drugs", vol. 89, No. 23, Dec. 4, 1978.

Chemical Abstracts, 105:130194p, "Binding of fluorinated 2-nitroimidazoles to spheroids and animal tumors", vol. 105, No. 15, Oct. 13, 1986.

Jerabek et al, "Synthesis and Biodistribution of $^{18}$F-Labeled Fluoronitroimidazoles: Potential in vivo Markers of Hypoxic Tissue", Appl. Radiat. Isot., vol. 37, No. 7, pp. 599–605, 1986.

Shitomoto, et al "Radiosensitization in vitro, etc." CA 105:186742h (1986).

Skorsgard et al, "Radiosensitizatio of Hypoxic, etc" CA 105: 168095v (1986).

Hinchliffe et al, "A Comparision of the, etc" CA 101: 225915f.

Watts et al, "A Comparison of the , etc" CA 107: 194204r (1987).

Workman et al, "Structure/Activity Relationships, etc" CA 98: 83220u (1983).

Sutherland et al I, "Cytotoxicity of Hypoxic, etc" CA 93: 18982b (1980).

Sutherland et al II, "Cytotoxicity of Hypoxic, etc" CA 95: 73188p (1981).

Brown et al I, "Factors Influencing, etc" CA 98: 122128s (1983).

Brown et al II, "Structure-Activity Relationships, etc" CA 96: 213378y (1982).

Takamuki et al, "Glutathione Depletion, etc" CA 109: 186390z (1988).

Reg. No. 117259-20-8.
Reg. No. 81892-69-5.
Reg. No. 81892-68-4.
Reg. No. 74141-75-6.
Reg. No. 22903-73-7.
Reg. No. 74141-74-5.
Reg. No. 22668-03-7.
Reg. No. 22668-01-5.

FIG. 1

FLUORINE-CONTAINING NITROIMIDAZOLE COMPOUNDS

This application is a continuation, of application Ser. No. 07/281,855 filed on Dec. 9, 1988, now abandoned, which is a continuation-in-part of application Ser. No. 07/204,367 filed on Jun. 9, 1988, now U.S. Pat. No. 4,927,941.

BACKGROUND OF THE INVENTION

1. Field of the Invention

The present invention relates to novel fluorine-containing nitroimidazole derivatives and a radiosensitizer comprising the same, more particularly, a radiosensitizer comprising a specific fluorine-containing nitroimidazole derivatives such as 2-nitroimidazole compound having a fluorine containing group at the 1-position, which facilitates inactivation of intractable hypoxic cells in malignant tumors by irradiation.

2. Description of the Related Art

To suppress reproduction or growth of malignant tumor cells, radiation exposure and administration of anti-tumor compounds or immunity substances are known and actually employed independently or in combination with surgical therapy. Among them, the radiation exposure has been employed for a long period of time.

A hypoxic cell sensitizer (or radiosensitizer) which is a drug for increasing sensitivity of the hypoxic cells against the radiation has been developed since it is promising means for increasing effects of radiotherapy.

Hitherto, various hypoxic cell sensitizers have been developed (cf. "Gan to Kagakuryoho" (Cancers and chemotherapy), Vol. 8, No. 11, November 1981, 1659).

1-(2-Nitro-1-imidazolyl)-3-methoxy-2-propanol (Misonidazole), which is one of typical hypoxic cell sensitizers, is about twice as effective as when no Misonidazole is used. However, it is hardly administered in an effective amount since it has strong neurotoxicity. No sensitizing effect was confirmed from the results obtained by administering it in human beings (cf. Reference 4 cited in the above "Gan to Kagakuryoho").

To increase sensitizing activity of the radiation and simultaneously to decrease the neurotoxicity, nitrotriazole derivatives and nitroimidazole derivatives have been studied (cf. Japanese Patent Kikai Publication Nos. 194019/1986 and 12763/1987). However, the conventional derivatives have insufficient radiosensitization.

It has been found that the radiosensitizing function of the azole compounds is attributed to their azole rings while the side chain contributes to their solubility in oils and pharmacological characteristics (Int. J. Radiat. Biol., 35, 1979, 151).

Compounds having a fluorine atom at a specific position in a molecule have been increasingly used as medicines because of mimic effects of the fluorine atom or modification of methabolic inhibition effect and solubility in oils (cf. "Kagakuno Ryoiki" (Chemical Fields), 35, 441 (1981)).

SUMMARY OF THE INVENTION

One object of the present invention is to provide a novel fluorine-containing nitroimidazole derivative having a partially or completely fluorinated substituent on its imidazole ring.

Another object of the present invention is to provide a fluorine-containing radiosensitizer which increases sensitivity of the hypoxic cells against radiation but has improved pharmacological characteristics and low toxicity and neurotoxicity.

Accordingly, the present invention provides a 2-nitroimidazole derivative of the formula:

(i)

wherein $R_f$ is a fluorine-containing organic group which has at least one fluorine atom on a carbon atom which bonds to the nitrogen atom of the imidazole ring or a carbon atom which bonds to said carbon atom.

DETAILED DESCRIPTION OF THE INVENTION

In the nitroimidazole derivative (i) of the present invention, $R_f$ is a group of the formula:

(ii)

wherein X is a hydrogen atom or a fluorine atom; Y is a fluorine atom, a chlorine atom, a trifluoromethyl group, a methyl group or a hydroxyl group, or X and Y together represent =O; Z is a hydrogen atom, a fluorine atom, a $C_1$-$C_5$ alkyl or fluoroalkyl group which may be substituted with hydroxyl, a group of the formula:

(iii)

wherein $R_1$ is a hydrogen atom or a $C_1$-$C_5$ alkyl or fluoroalkyl group, E is a hydrogen atom or a fluorine atom and m is 0 or 1, (iv)

wherein $R_2$ is a $C_1$-$C_5$ alkyl or fluoroalkyl group, (v)

wherein $R_3$ and $R_4$ are the same or different and a hydrogen atom, a hydroxyl group or a $C_1$-$C_5$ alkyl or fluoroalkyl group which may be substituted with a hydroxyl group, a $C_1$-$C_5$ alkoxy group or an amide group, or $R_3$ and $R_4$ forms a 3 to 6 membered ring together with the nitrogen atom to which they bond, and E and m are the same as defined above, (vi)

wherein R₃, R₄, E and m are the same as defined above, (vii)

wherein R₃, R₄, E and m are the same as defined above, (viii)

wherein R₃, R₄, E and m are the same as defined above,

—(CHE)$_m$—A—R₅   (ix)

wherein A is an oxygen atom or a sulfur atom, R₅ is a hydrogen atom, a C₁-C₅ alkyl or fluoroalkyl group which may be substituted with a hydroxyl group, a C₁-C₅ alkoxyl group or a C₁-C₅ oxyacyl group, a group of the formula: —CO—R₆ in which R₆ is a C₁-C₅ alkyl group, (x)

wherein R₇ is a C₁-C₇ alkylene group, R₈ is a C₁-C₃ alkyl group and A is the same as defined above, or

(xi)

wherein R₅ is a C₁-C₅ alkyl or fluoroalkyl group and E and m are the same as defined above. Y and Z may together form =CF—CF₃ or =CHOR₆ in which R₆ is the same as defined above. n is 0 or 1. However, R$_f$ is not —CH₂—CH₂F.

Preferred examples of the group R$_f$ are as follows:

| | |
|---|---|
| —CH₂CF₂COOCH₃ | (1) |
| —CH₂CF₂CONHCH₂CH₂OCH₃ | (2) |
| —CH₂CF₂CONHCH₂CH₂OH | (3) |
| —CH(CH₃)—CH₂CONH(CH₂)₂OCH₃ | (4) |
| —CH(CF₃)—CH₂COOCH₃ | (5) |
| —CH₂CH(OH)CH₂OCH₂CF₂CF₂H | (6) |
| —CH₂CHFCH₂OCH₃ | (7) |
| —CH₂CHFCH₂OCOCH₃ | (8) |
| —CH₂CHFCH₂OH | (9) |
| —CH₂CH=CHOCH₂CF₃ | (10) |
| —CF=CFCF₃ | (11) |
| —CF₂CF₂H | (12) |
| —CH₂CHFCONH(CH₂)₂OH | (14) |
| —CH₂CF₃ | (15) |
| —CH₂CF₂COCH₃ | (16) |
| —CH₂COCF₃ | (17) |
| —CH₂COCHF₂ | (18) |
| —CH₂COCH₂F | (19) |

(20)

(21)

(22)

(23)

(24)

| | |
|---|---|
| —CH₂CF₂CH₂OH | (25) |

(26)

| | |
|---|---|
| —CH₂CF₂CH₂SCH₃ | (27) |
| —CF₂CONH(CH₂)₂OH | (28) |

(29)

(30)

(31)

(32)

| | |
|---|---|
| —CHF₂ | (33) |
| —CONH(CH₂)₃CF₃ | (34) |
| —CH₂CH₂CHF₂ | (35) |

-continued

—CH₂F (36)

—CH₂CHFCOOCH₃ (37)

—CH₂CHFCONHCH₂CH₂OCH₃ (38)

—CH₂CF₂CH₂NH₂ (39)

—CH₂CF₂CH₂NHCOCH₃ (40)

—CH₂CF₂CH₂NHCOCH₂CH₂OH (41)

(42)

—CH₂CF₂CONH₂ (43)

—CH₂CF₂CONHOH (44)

—CH₂CF₂CONHCH₂CH₂NH₃Cl (45)

—CH₂CF₂CH₂NHCH₂CH₂OCH₃ (46)

—CH₂CHFCONHCH₂CH₂OH (47)

—CH₂CF₂CONHCH₂CH₃ (48)

—CH₂CF₂CONHCH₂CH₂CH₃ (49)

—CH₂CF₂CONH(CH₂)₅CH₃ (50)

—CH₂CF₂CONHCH₂CF₃ (51)

—CH₂CF₂CONH(CH₂)₃CF₃ (52)

—CH₂CF₂CONHCH(CH₃)₂ (53)

—CH₂CF₂CONHC(CH₃)₃ (54)

(55)

—CH₂CF₂CONH(CH₂)₂OCH₂CH₃ (56)

—CH₂CF₂CONH(CH₂)₃OCH₂CH₃ (57)

—CH₂CF₂CONH(CH₂)₃OCH₃ (58)

—CH₂CF₂CONH(CH₂)₃OH (59)

—CH₂CF₂CONHCH₂CH(OH)CH₃ (60)

—CH₂CF₂CONH(CH₂)₂O(CH₂)₂OH (61)

—CH₂CHFCH₂OCH₂CH₂OCH₃ (63)

—CH₂CHFCH₂OCH₂CH——CH₂ (64)
                                      O    O
                                         \  /
                                          C
                                       /   \
                                 H₃C     CH₃

—CH₂CHFCH₂OCH₂CH(OH)CH₂OH (65)

CH₂OCOCH₃ (66)
                    /
—CH₂CHFCH₂OCH
                    \
                     CH₂OCOCH₃

CH₂OH (67)
                /
—CH₂CHFCH₂OCH
                \
                 CH₂OH

—CH₂CHFCH₂OCH₂CH₂OH (68)

(69)

The nitroimidazole derivative (i) of the present invention may be prepared as follows:

(A) When R$_f$ is a fluoroalkyl group:

(1) A fluorine-containing epoxy compound is addition reacted with 2-nitroimidazole to form a fluoroalkyl group having a hydroxyl group as the group R$_f$.

The reaction temperature is from 0° to 100° C., preferably from 50° to 70° C. Although no solvent is required, the reaction may be carried out in a solvent such as alcohol, dioxane and the like.

(2) The hydroxyl group in the compound obtained in the above (1) is fluorinated with a suitable fluorinating agent (e.g. diethylaminosulfatrifluoride (DAST)).

The reaction is carried out in an aprotic solvent (e.g. methylene chloride, chloroform and ether) at a temperature of 0° to 50° C.

(3) A fluoroolefin is addition reacted with 2-nitroimidazole.

This addition reaction is carried out in an aprotic solvent (e.g. acetonitrile and dimethylformamide) in the presence of a base at a temperature of 0° to 100° C.

(B) When R$_f$ is a fluoroester group:

(1) A fluorine-containing α,β-unsaturated carbonyl compound is addition reacted with 2-nitroimidazole.

The reaction is carried out in an aprotic solvent (e.g. dioxane and tetrahydrofuran) in the presence of an acid or a base at a temperature of 30° to 120° C.

(2) A fluorooxetane is addition reacted with 2-nitroimidazole.

The reaction is carried out in an alcohol (e.g. methanol and ethanol) at a temperature of 0° to 50° C.

(C) When R$_f$ is a fluorine-containing amide group;

The compound prepared in (B) is further reacted with an amine.

This reaction is carried out in the absence of a solvent at a temperature of 0° to 100° C.

(D) When R$_f$ is a fluorine-containing amine group:

(1) The compound prepared in (C) is reduced with a suitable reducing agent. Any reducing agent that does not reduce the nitro group can be used. For example, B₂H₆ is preferred. Any solvent that does not deactivate the reducing agent may be used. For example, tetrahydrofuran and dioxane are used.

(E) When R$_f$ is a fluorine-containing amide group:

(1) The compound prepared in (D) is reacted with carboxylic halide, carboxylic anhydride or lactone. A solvent is not necessarily required. When the carboxylic anhydride is used, a base catalyst such as pyridine or morpholine may be used.

Among the above preparation reactions, typical reactions are represented by following reaction schemes:

(A)-(1):

-continued

(A)-(2):

(A)-(3):

(B)-(1):

(B)-(2):

(C)-(1):

(D)-(1):

(E)-(1):

In the above formulas, $R^1$ and $R^2$ are independently a hydrogen atom or a lower alkyl group, X is a halogen atom, and "NI" means 2-nitroimidazol-1-yl.

The nitroimidazole derivative (i) of the present invention is useful as a radiosensitizer. Its dose depends on the types of tumor and/or the compound (i). Generally, it is from 20 to 10,000 mg in case of oral administration, from 0.5 to 10,000 mg in case of injection or 20 to 10,000 mg in case of suppository. An optimum dose may be determined by a medical practitioner according to symptom based on a kind of radiation, a radiation dose, fractionation of irradiation and the like.

The nitroimidazole compound (i) of the present invention may be administered in any suitable form. The compound (i) may be compounded with any carrier which is conventionally used in this field, and formulated by a conventional method.

The present invention is further illustrated by the following Preparation Examples for the nitroimidazole derivatives (i) and Examples showing the radiosensitization effect of the derivatives (i).

In Examples, "NI" means 2-nitroimidazol-1-yl.

PREPARATION EXAMPLE 1

$$NI-CH_2CF_2COOCH_3 \quad (1)$$

To 1.0 g (8.8 mmol) of 2-nitroimidazole and 2.0 g (19 mmol) of sodium carbonate, 20 ml of methanol was added. To the obtained mixture, 1.8 g (14 mmol) of tetrafluorooxetane was dropwise added. After stirring for 30 minutes at room temperature, the mixture was concentrated and partitioned between ethyl acetate and water. The ethyl acetate phase was dried on magnesium sulfate and filtered. The filtrate was concentrated and subjected to isolation and purification by silica gel column chromatography to give 1.48 g of methyl 3-(2'-nitroimidazol-1'-yl)-2,2-difluoropropionate as an oil.

$^1$H-NMR (CDCl$_3$): $\delta$=3.89 (3H, s, —OCH$_3$), 5.26 (2H, t, —NCH$_2$, $J_{HF}$=14 Hz), 7.21 (2H, s, H$_4'$, H$_5'$).

$^{19}$F-NMR (standard: TFA): 30.9.

PREPARATION EXAMPLE 2

$$NI-CH_2CF_2CONHCH_2CH_2OCH_3 \quad (2)$$

To a solution of 1.74 g (7.40 mmol) of methyl 3-(2'-nitroimidazol-1'-yl)-2,2-difluoropropionate in 5.0 ml of dioxane, 2.0 ml (23 mmol) of 2-methoxyethylamine was drop-wise added and stirred at room temperature for 1 hour.

After reaction, the solution was concentrated and subjected to isolation and purification by silica gel column chromatography to give 1.75 g of 3-(2'-nitroimidazol-1'-yl)-2,2-difluoropropionate acid methoxyethylamide as an oil.

$^1$H-NMR (CDCl$_3$): $\delta$=3.36 (3H, s, —CH$_3$), 3.45–3.58 (4H, m, —CH$_2$—CH$_2$—O—), 5.22 (2H, t, H$_1'$, $J_{HF}$=14 Hz), 6.94 (1H, bs, —CONH—), 7.18–7.27 (2H, m, H$_4$, H$_5$).

$^{19}$F-NMR (CDCl$_3$; standard: TFA): 32.0.

PREPARATION EXAMPLE 3

$$NI-CH_2CF_2CONHCH_2CH_2OH \quad (3)$$

To a solution of 1.49 g (6.34 mmol) of methyl 3-(2'-nitroimidazol-1'-yl)-2,2-difluoropronionate in 4.0 ml of methanol, 0.40 ml (6.6 mmol) of ethanol amine was added and stirred for 30 minutes at room temperature. After concentrating the reaction solution with an evaporator, the concentrate was partitioned between ethyl acetate and saturated saline. The ethyl acetate layer was dried on magnesium sulfate and filtered. The filtrate was concentrated and crystallized from ethanol to give 1.00 g (3.80 mmol) of needle shape crystalline 3-(2'-nitroimidazolyl)-2,2-difluoropropionic acid hydroxyethylamide. m.p. 108.0°–110.0° C.

$^1$H-NMR (CDCl$_3$): $\delta$=3.39–3.62 (2H, m, —NHCH$_2$—), 3.67–3.88 (2H, m, —CH$_2$—O), 5.22 (2H, t, H$_3$, $J_{HF}$=14 Hz), 6.94 (1H, bs, —CONH—), 7.21 (2H, s, H$_4'$, H$_5'$).

$^{19}$F-NMR (CDCl$_3$; standard: TFA): 31.9.

PREPARATION EXAMPLE 4

$$NI-CH_2CHFCH_2OCH_3 \quad (7)$$

To a solution of 914 mg (4.54 mmol) of 1-(2'-hydroxy-3'-methoxypropyl)-2-nitroimidazole in 5.0 ml of dry dioxane, 1.00 g (6.20 mmol) of DAST was dropwise added with cooling by ice and then reacted for 2 hours at room temperature with stirring. After reaction, to the solution, 5.0 ml of ethanol was added to decompose excess DAST. The solution was then concentrated and subjected to isolation and purification by silica gel column chromatography to give 480 mg of 1-(2-'-fluoro-3'-methoxypropyl)-2-nitroimidazole.

m.p. 39.0°–44.0° C.

$^1$H-NMR (CDCl$_3$): δ=3.44 (3H, s, —OCH$_3$), 3.58 (1H, dd, H$_{3'a}$, $J_{H3'a-H2'}$=3Hz, $J_{H3'a-F}$=3 Hz), 3.80 (1H, d, H$_{3'b}$, $J_{H3'b-F}$=3 Hz), 4.32–4.56 (1H, m, H$_{1'a}$), 4.65–4.72 (1H, m, H$_{1'b}$).

$^{19}$F-NMR (CDCl$_3$; standard: TFA): 113.6.

PREPARATION EXAMPLE 5

NI—CH$_2$CHFCH$_2$OCOCH$_3$ (8)

To a solution of 3.93 g (17.1 mmol) of 1-(2'-hydroxy-3'-acetoxypropyl)-2-nitroimidazole in 30 ml of dry dioxane, 4.00 g of DAST was dropwise added with stirring and cooling by ice. After addition, the mixture was reacted for 5 hours at room temperature with stirring. Thereafter, to the solution, 10 ml of ethanol was added to decompose excess DAST. The solution was then concentrated and partitioned between chloroform and an aqueous solution of sodium hydrogen carbonate. The chloroform phase was dried on magnesium sulfate and filtered. The filtrate was concentrated and subjected to isolation and purification by silica gel column chromatography to give 1.15 g of 1-(2'-fluoro-3'-acetoxypropyl)-2-nitroimidazole.

$^1$H-NMR (CDCl$_3$): δ=2.15 (3H, s, —COCH$_3$), 4.12–5.18 (4H, m, H$_{1'}$, H$_{3'}$), 5.05 (1H, dm, H$_{2'}$, $J_{H2'-F}$=48.0 Hz), 7.19–7.26 (2H, m, H$_4$, H$_5$).

$^{19}$F-NMR (CDCl$_3$; standard: TFA): 113.6.

PREPARATION EXAMPLE 6

NI—CH$_2$CHFCH$_2$OH (9)

To 910 mg (3.94 mmol) of 1-(2'-fluoro-3'-acetoxypropyl)-2-nitroimidazole, 6N-HCl was added and stirred overnight at room temperature. The reaction mixture was concentrate and subjected to isolation and purification by silica gel column chromatography to give 280 mg of 1-(2'-fluoro-3'-hydroxypropyl)-2-nitroimidazole.

m.p. 84.0°–89.0° C.

$^1$H-NMR (CDCl$_3$+DMSO-d$_6$): δ=3.48–3.97 (2H, m H$_{3'}$), 4.52–5.24 (3H, m, H$_{1'}$, H$_{2'}$), 7.19 (1H, s, H$_5$), 7.42 (1H, s, H$_4$).

$^{19}$F-NMR (CDCl$_3$+DMSO-d$_6$; standard: TFA): 114.5.

PREPARATION EXAMPLE 7

NI—CH$_2$CF$_2$CH$_2$OH (25)

To a solution of 4.00 g (15.1 mmol) of 3-(2'-nitroimidazol-1'-yl)-2,2-difluoropropionic acid in 50 ml of dry THF (tetrahydrofuran) cooled to −40° C., 1.20 g (30.4 mmol) of NaBH$_4$ was gradually added in a nitrogen stream and then 7.6 ml (60 mmol) of BF$_3$O(C$_2$H$_5$)$_2$ was gradually added. After addition, the reaction mixture was stirred for one hour while cooling by ice, neutralized with dilute hydrochloric acid and extracted with ethyl acetate. The extract was dried on magnesium sulfate and filtered. The filtrate was concentrated and subjected to isolation and purification by silica gel column chromatography to give 510 mg of 1-(2',2'-difluoro-3'-hydroxypropyl)-2-nitroimidazole.

$^1$H-NMR (CDCl$_3$): δ=3.88 (2H, t, H$_{3'}$, $J_{H3'-F}$=12 Hz), 5.08 (1H, t, H$_{1'}$, $J_{H1'-F}$=12 Hz), 7.22–7.30 (2H, m, H$_4$, H$_5$).

$^{19}$F-NMR (CDCl$_3$; standard: TFA): 33.5.

PREPARATION EXAMPLE 8

NI—CH$_2$CF$_2$CONHOH (44)

To a solution of 3.0 g (12.8 mmol) of methyl 3-(2'-nitroimidazol-1'-yl)-2,2-difluoropropionate in 30 ml of methanol, 1.0 (18.7 mmol) of hydroxyamine hydrochloride was suspended. To the suspension, a solution of 1.0 g of potassium hydroxide in 20 ml of methanol was gradually dropwise added followed by reaction for 3 hours at room temperature.

The precipitate was filtrated off. The filtrate was concentrated and subjected to isolation and purification by silica gel column chromatography to give 160 mg of 3-(2'-nitroimidazol-1'-yl)-2,2-difluoropropionylhydroxyamide.

$^1$H-NMR (CD$_3$OD): δ=5.32 (2H, t, H$_3$, $J_{H3-F}$=15 Hz), 7.22 (1H, m, H$_5$), 7.52 (1H, s, H$_4$).

$^{19}$F-NMR (CD$_3$OD; standard: TFA): 34.5.

PREPARATION EXAMPLE 9

NI—CH$_2$CF$_2$CONHCH$_2$CH(OH)CH$_3$ (60)

To a solution of 1.0 g of methyl 3-(2'-nitroimidazol-1'-yl)-2,2-difluoropropionate in 30 ml of dioxane, 1,0 g of 2-hydroxypropylamine was added and reacted at room temperature for 3 hours. Then, the reaction mixture was concentrated and subjected to isolation and purification by silica gel chromatography to give 530 mg of 3-(2'-nitroimidazol-1'-yl)-2,2-difluoropropionyl-(2''-hydroxypropyl)amide.

$^1$H-NMR (DMSO-d$_6$; standard: TMS): δ=1.09 3H, d, —CH$_3$, $J_{H2''-H3''}$=5Hz), 3.16 (2H, t, —NCH$_3$, $J_{H1''-H2''}$=$J_{H1''-NH}$=6 Hz) 3.80 (1H, m, CH—O—), 4.88 (1H, d, —OH, $J_{H2''-OH}$=5 Hz), 5.36 (2H, t, CH$_2$CF$_2$, $J_{H1-F}$=15 Hz), 7.38 (1H, d, H$_{5'}$, J=1 Hz), 7.78 (1H, s, H$_{4'}$), 9.04 (1H, t, NH, $J_{HNH-H1''}$=4 Hz).

$^{19}$F-NMR (DMSO-d$_6$; standard: TFA): 31.0.

PREPARATION EXAMPLE 10

NI—CH$_2$CHFCH$_2$N◯.HCl (69)

To a solution of 2.2 g (8.65 mmol) of 1-(2'-hydroxy-3'-piperidylpropyl)-2-nitroimidazole in 20 ml of dry dioxane, 2.5 g (15.5 mmol) of DAST was dropwise added with cooling by ice and reacted for 5 hours at room temperature. After reaction, to the solution, 10 ml of methanol was added to decompose excess DAST. Then, the solution was concentrated and partitioned between chloroform and water. The pH of the aqueous phase was adjusted to 12 by the addition of an aqueous solution of sodium hydroxide and the liquid was again partitioned between chloroform and water. The chloroform phase was dried on magnesium sulfate and filtered. The filtrate was concentrated and subjected to isolation and purification by silica gel chromatography to give 1-(2'-fluoro-3'-piperidylpropyl)-2-nitroimidazole, which was treated with hydrochloric acid to form a hydrochloride and crystallized from ethanol to give 560 mg of crystalline hydrochloride of 1-(2'-fluoro-3'-piperidylpropyl)-2-nitroimidazole.

$^1$H-NMR (DMSO-d$_6$): δ=1.22–2.18 (6H, m, piperidyl), 2.88–3.65 (4H, m, piperidyl), 3.50–3.98 (2H, m, H$_3'$), 4.72–4.88 (1H, m, H$_{1'a}$), 5.00–5.13 (1H, m, H$_{1'b}$), 5.76 (1H, dm, H$_{2'}$, J$_{H2'-F}$=51 Hz), 7.38 (1H, d, H$_5$, J$_{H5-H4}$=1.0 Hz), 78.6 (1H, d, H$_4$, J$_{H4-H5}$=1.0 Hz).

$^{19}$F-NMR (DMSO-d$_6$; standard: TFA): 106.1.

EXAMPLE 1

Radiosensitization effect on cells (ER in vitro)

To examine the in vitro radiosensitization effect of the present nitroimidazole derivative (i), 100,000 cells of Chinese hamster V-79 cells were cultured in monolayer in a culture dish, and the V-79 cells in a log phase were prepared.

A solution of a predetermined concentration of a compound to be examined in a medium was added to the dish. After standing for 60 minutes at 37° C., the dish was placed in a closed vessel at room temperature. Then, the vessel was purged with nitrogen for 10 minutes to exclude oxygen and X-ray was irradiated at a dose rate of 1.6 Gy/min.

After the irradiation, the cells were washed with phosphate buffer and digested with trypsin into single cells. Then, a predetermined amount of the cells was introduced into 5 ml of a culture medium in a culture dish and cultured for 7 days at 37° C. After staining and washing with water, the number of colonies formed was counted.

The results are shown in following Table 1 as ER in vitro.

EXAMPLES 2

Radiosensitization effect on tumor transplanted in animal (ER in vivo)

To both thighs of male Balb/c mouse (8 weeks; 4 mice in a group), 10$^5$ of EMT-6 tumor cells were subcutaneously inoculated. After the diameter of the tumor reached about 1 cm, a solution of a compound to be examined in saline at a predetermined concentration was intraperitonealy administered. After the time at which the maximum concentration in the tumor (shown in Table 1) was reached, X-ray was irradiated at 4.5 Gy/min. for 5 minutes and then the mouse was sacrificed.

After the mouse was systemically sterilized with 70% ethanol, the tumor was taken out and the tissue was homogenized. Then, 22 ml of trypsin was added to the homogenate and stirred for 50 minutes at 37° C. The number of cells in the supernatant was counted. A predetermined amount of the cells was introduced in a plastic plate having a diameter of about 5 cm. To the plate, 5 ml of medium was added and cultured in a CO$_2$ incubator. The plates containing the irradiated and unirradiated cells were removed from the incubator after 9 days and 10 days incubation, respectively. The cells were fixed by methanol and stained by Giemsa stain. Then, the number of colonies formed were counted.

Figure 1:
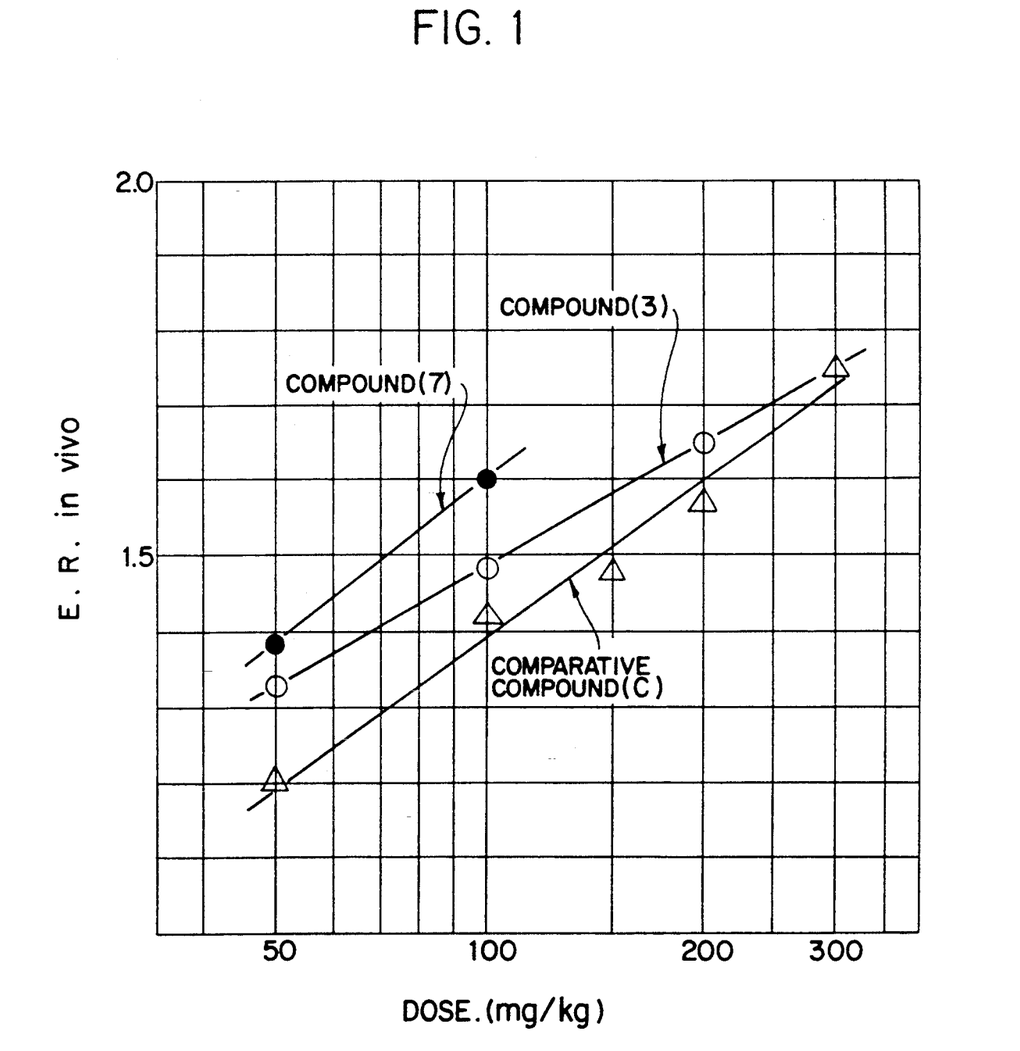
FIG. 1 is a graph showing the relationship between ER in vivo and doses of the compounds (3) and (7) and the comparative compound (c)

The survival rate was calculated with using the unirradiated cells as control. The results are shown as ER in vivo in following Table 1. In addition, the relationship between the administered amount of the compounds (3) or (7) or the comparative compound (c) (Misonidazole) and the ER in vivo is shown in FIG. 1.

TABLE 1

| Compound | R$_f$ | ER in vitro (mM) | ER in vivo (mg/kg) [min.][2] | LD$_{50}$[1] (g/kg) |
|---|---|---|---|---|
| (1) | —CH$_2$CF$_2$COOCH$_3$ | 1.40 (1.0) | — | — |
| (2) | —CH$_2$CF$_2$CONH(CH$_2$)$_2$OCH$_3$ | 1.61 (1.0) | 1.26 (100) | — |
| (3) | —CH$_2$CF$_2$CONH(CH$_2$)$_2$OH | 1.58 (1.0) | 1.48 (100) [20] | 2.3 |
| (7) | —CH$_2$CHFCH$_2$OCH$_3$ | 1.62 (1.0) | 1.60 (100) | 0.4 |
| (9) | —CH$_2$CHFCH$_2$OH | 1.58 (1.0) | 1.58 (100) | — |
| (25) | —CH$_2$CF$_2$CH$_2$OH | 1.55 (1.0) | 1.44 (100) [30] | 0.4 |
| (44) | —CH$_2$CF$_2$CONHOH | 1.46 (1.0) | 1.25 (100) | — |
| (60) | —CH$_2$CF$_2$CONHCH$_2$CH(OH)CH$_3$ | 1.49 (1.0) | 1.12 (100) [20] | — |
| (69) | —CH$_2$CHFCH$_2$N(piperidyl)·HCl | 1.78 (1.0) | 1.45 (100) | — |
| Comparative (a) | —CH$_2$CHCl(OH) | 1.78 (1.0) | 1.50 (200) | — |
| Comparative (b) | —CH$_2$CHCH$_2$F(OH) | 1.77 (1.0) | 1.50 (200) | — |

TABLE 1-continued

| Compound | $R_f$ | ER in vitro (mM) | ER in vivo (mg/kg) [min.][*2)] | $LD_{50}$[*1)] (g/kg) |
|---|---|---|---|---|
| Comparative (c) | —CH$_2$CHCH$_2$OCH$_3$<br>\|<br>OH<br>(Misonidazole) | — | 1.42 (100) [20] | 1.3 |

Note:
[*1)] For determination of $LD_{50}$, female ICR mice of 5 weeks were used.
[*2)] The time at which the maximum concentration in the tumor was reached. In Examples in which no time was indicated, X-ray was irradiated after 40 minutes from administration.

EXAMPLE 3

Evaluation of radiosensitization effect through the Growth Delay method.

To a right thigh of female C3H mouse (8 weeks, 6 to 10 mice in a group), SCC VII tumor cells were subcutaneously inoculated. After about two weeks at which the tumor reached 10 mm, a solution of a compound to be examined in saline at a predetermined concentration was intraperitonealy administered (100 mg of the compound per kg). After 20 to 40 minutes from the administration, X-ray was irradiated at 4.5 Gy/min.

Every day, a longest radius (a) and a shortest radius (b) of the tumor were measured and the size of the tumor was calculated according to the following equation:

$$A_x = \frac{\pi \times a \times b}{4}$$

The calculated value $A_x$ was divided by the value before irradiation $A_0$ to obtain a relative volume $A_x/A_0$. The relative volume for each group were averaged and plotted against the observation period (days). From the obtained curve, the number of days at which $A_x/A_0$ is 2 ($\tau_2$, days) was calculated. From this value, a sensitization effect ratio (SER) was calculated for the case in which the sensitizer was used. The results when the compound (3) or the comparative compound (c) was used are shown in Table 2.

TABLE 2

| Treatment | $\tau$ (days) | SER |
|---|---|---|
| (None) | 4.5 | — |
| Irradiation (20 Gy) | 8.0 | 1.00 |
| Irradiation (30 Gy) | 12.8 | 1.50 |
| Comparative compound (c) + Irradiation (20 Gy) | 14.7 | 1.59 |
| Compound (3) + Irradiation (20 Gy) | 17.3 | 1.87 |
| Irradiation (40 Gy) | 20.0 | 2.00 |

EXAMPLE 4

Distribution of the radiosensitizer in a mouse body

Figure 2A:
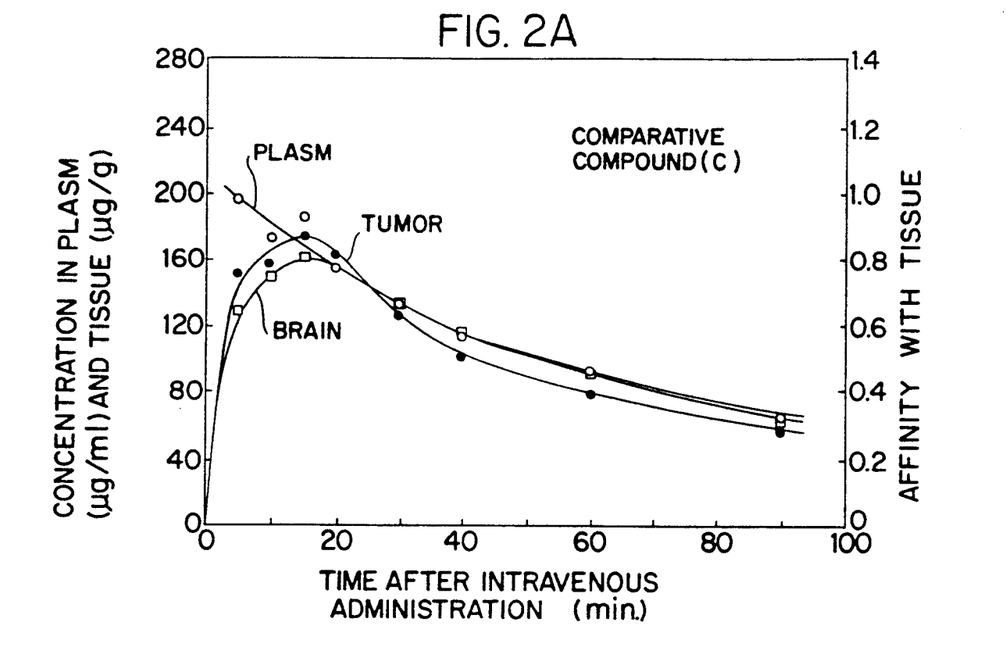
FIGS. 2A-B are graphs showing the relationships between the concentration of the administered compounds in plasma and tissue and the time after intravenous administration.
Figure 2B:
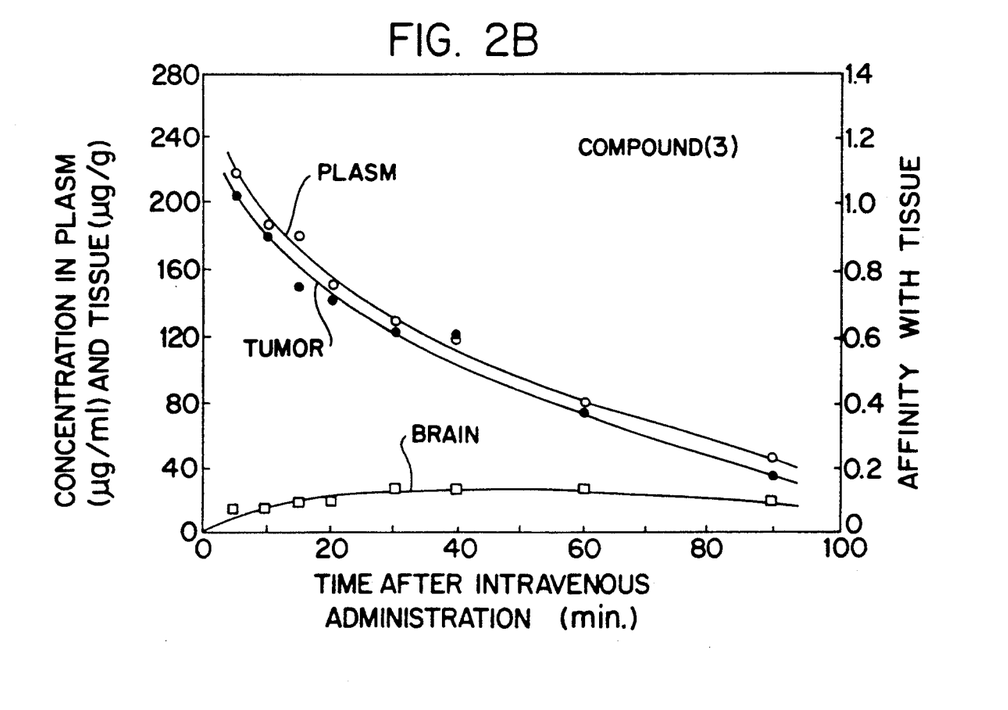

To a right thigh of each of eight female C3H mice (8 weeks), SCC VII tumor cells were subcutaneously inoculated. After about two weeks at which the tumor reached 10 mm, a solution of a compound to be examined in saline at a predetermined concentration was intravenously administered (for example, 200 mg of the compound per kg). After 5, 10, 15, 20, 30, 40, 60 and 90 minutes from the administration, an amount of blood was sampled from the eye socket and then the mice were sacrificed. The tumor and the brain were taken out and weighed. They were homogenized in 10 time volume of pure water. Then, to the homogenate, methanol of two time volume of the homogenate was added and thoroughly stirred followed by centrifugation. The supernatant was analyzed with chromatography to find the distribution of the compound in each organ. The results for the compound (3) and the comparative compound (c) are shown in FIG. 2.

What is claimed is:

1. A 2-nitroimidazole derivative of the formula:

(i)

wherein $R_f$ is a group of the formula:

(ii)

wherein X is a fluorine atom; Y is a fluorine atom, a chlorine atom, a trifluoromethyl group, a methyl group or a hydroxyl group, or X and Y together represent =O; Z is a group of the formula:

(v)

wherein R$_3$ and R$_4$ are the same or different and are each a hydrogen, a hydroxy group a C$_1$-C$_5$ alkyl or fluoroalkyl group, a hydroxy group or a C$_1$-C$_5$ alkoxy group substituted C$_1$-C$_5$ alkyl or fluoroalkyl group, or R$_3$ and R$_4$ forms a 3 to 6 member ring together with the nitrogen atom to which R$_3$ and R$_4$ bond, E is a hydrogen atom or a fluorine atom and m is 0 or 1, or (vi)

wherein R$_3$, R$_4$, E and m are the same as defined above.

* * * * *